(12) United States Patent
Kutyavin

(10) Patent No.: US 8,637,276 B2
(45) Date of Patent: Jan. 28, 2014

(54) METHODS, COMPOSITIONS AND KITS FOR THE IMPROVED DETECTION OF SMALL RNA MOLECULES

(76) Inventor: Igor Vassily Kutyavin, Woodinville, WA (US)

(*) Notice: Subject to any disclaimer, the term of this patent is extended or adjusted under 35 U.S.C. 154(b) by 505 days.

(21) Appl. No.: 12/682,344

(22) PCT Filed: Oct. 8, 2008

(86) PCT No.: PCT/US2008/079169
§ 371 (c)(1),
(2), (4) Date: Aug. 17, 2010

(87) PCT Pub. No.: WO2009/048928
PCT Pub. Date: Apr. 16, 2009

(65) Prior Publication Data
US 2010/0304442 A1     Dec. 2, 2010

Related U.S. Application Data

(60) Provisional application No. 60/978,657, filed on Oct. 9, 2007.

(51) Int. Cl.
| | |
|---|---|
| *C12P 19/34* | (2006.01) |
| *C12Q 1/68* | (2006.01) |
| *C07H 21/04* | (2006.01) |
| *B01L 3/00* | (2006.01) |
| *C07G 3/00* | (2006.01) |

(52) U.S. Cl.
USPC ............. 435/91.1; 435/6.1; 435/9.2; 536/4.1; 536/23.1; 536/24.3; 422/430

(58) Field of Classification Search
USPC ........ 435/6.1, 91.1, 91.2; 536/4.1, 23.1, 24.3; 422/430
See application file for complete search history.

(56) References Cited

U.S. PATENT DOCUMENTS 6,218,118 B1 * 4/2001 Sampson et al. .................. 506/4

FOREIGN PATENT DOCUMENTS

| WO | WO 01/64958 A2 | 9/2001 |
| WO | WO 2005/098029 A2 | 10/2005 |
| WO | WO 2007/127992 A2 | 11/2007 |

OTHER PUBLICATIONS

Kuwahara et al. Bioorganic and Medicinal Chemistry Letters 13 (2003) 3735-3738.*
Graham et al., "DNA duplexes stabilized by modified monomer residues: synthesis and stability," *J. Chem. Soc., Perkin Trans. 1*: 1131-1138, 1998.
Seela et al., "The Influence of Modified Purine Bases on the Stability of Parallel DNA," *Bioorganic & Medicinal Chemistry Letters 10*: 289-292, 2000.

* cited by examiner

*Primary Examiner* — Jezia Riley
(74) *Attorney, Agent, or Firm* — Seed IP Law Group PLLC

(57) ABSTRACT

The present invention provides compositions, methods and kits for use in the detection of small RNA sequences, which allow for rapid and robust amplification and detection. The methods provide improved sensitivity and efficiency in the amplification-based detection of small RNA sequences by incorporating one or more base-modified duplex-stabilizing dNTPs during reverse transcription and/or amplification.

17 Claims, 2 Drawing Sheets

Forward primer (Tm = 71 °C)

5'-GAGACCAGCATGCGTTTAATGCTAATC miR-155

5'-UUAAUGCUAAUCGUGAUAGGGG-3'

CACTATCCCCTTGAGCTAGGATCG-5'

Reverse primer (Tm = 72 °C)

A is 2,6-diaminopurine
Underlined are primers artificial tail sequences

PCR primer design for detection of miR-155

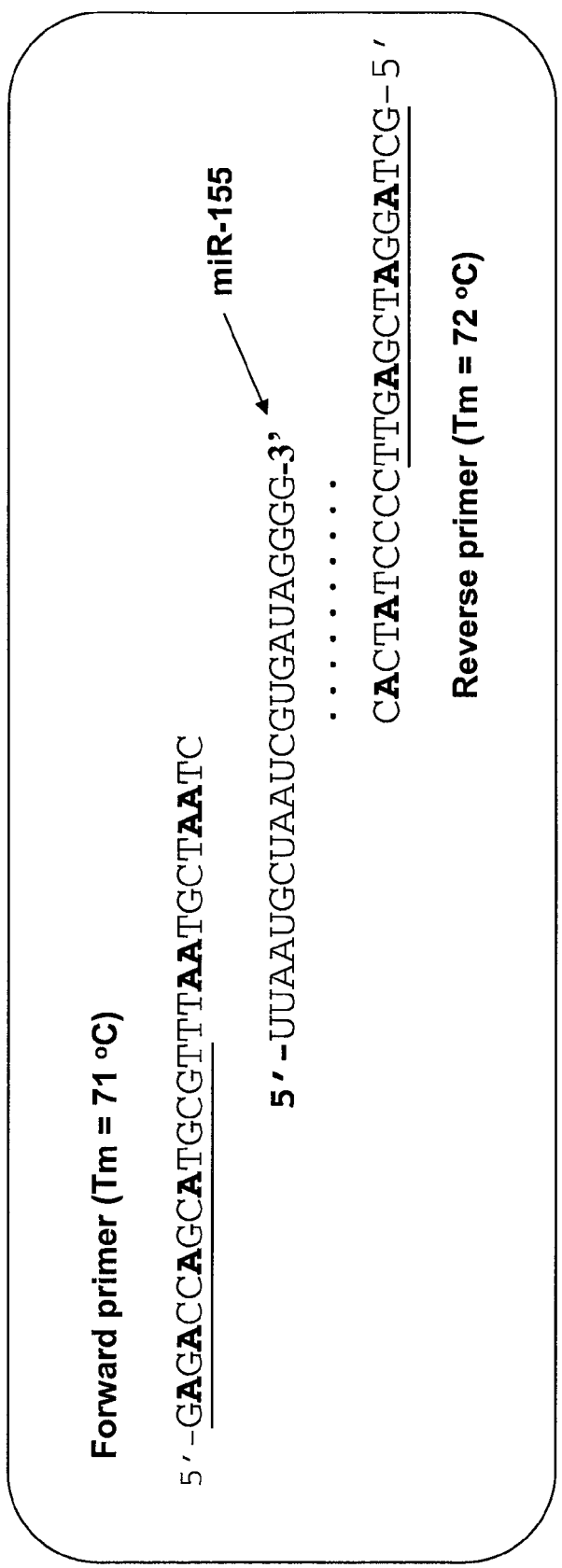
Figure 1 – PCR primer design for detection of miR-155

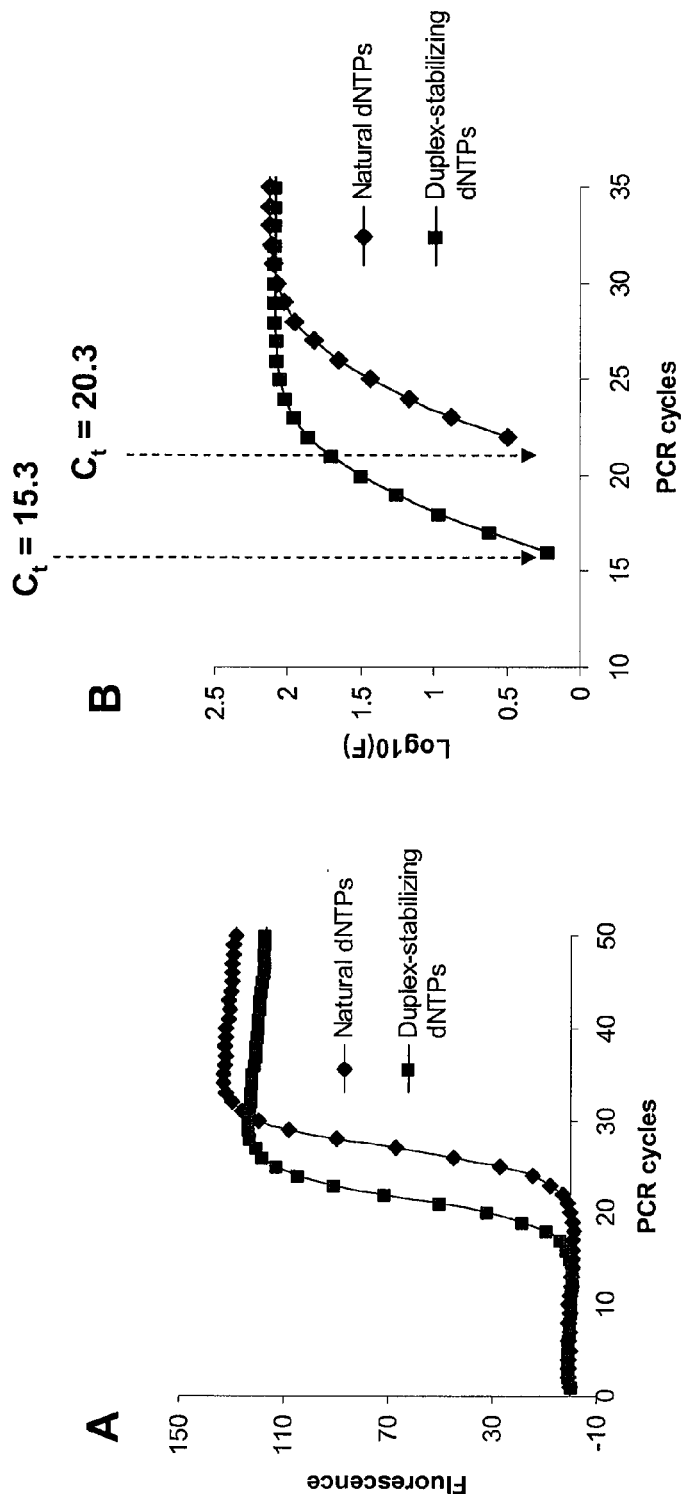
Figure 2 - Improvement in PCR efficiency and sensitivity of miRNA detection using base-modified duplex-stabilizing dNTPs during Reverse Transcription reaction (cDNA synthesis)

METHODS, COMPOSITIONS AND KITS FOR THE IMPROVED DETECTION OF SMALL RNA MOLECULES

CROSS-REFERENCE TO RELATED APPLICATIONS

This application is a U.S. National Phase Application of International Application No. PCT/US2008/079169, filed Oct. 8, 2008; which claims the benefit under 35 U.S.C. 119(e) of U.S. Provisional Patent Application No. 60/978,657, filed Oct. 9, 2007. These applications are incorporated herein by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200155_405USPC_SEQUENCE_LISTING.txt. The text file is 1 KB, was created on Aug. 17, 2010, and is being submitted electronically via EFS-Web.

BACKGROUND OF THE INVENTION

The present invention relates to improved methods, compositions and kits for the detection of RNA molecules. More particularly, the invention relates to the use of base-modified, duplex-stabilizing nucleoside triphosphates in reverse transcription reactions for improving duplex stability during subsequent amplification-based detection of short RNA sequences, such as miRNA.

Micro RNAs (miRNAs) are a highly conserved class of small RNA molecules that are transcribed from DNA but are not translated into protein. miRNAs are processed into single stranded ~17-24 nucleotide (nt) molecules that become incorporated into the RNA-induced silencing complex (RISC) and have been identified as key regulators of development, cell proliferation, apoptosis and differentiation. RISC mediates down-regulation of gene expression through translational inhibition, transcript cleavage, or both. RISC is also implicated in transcriptional silencing in the nucleus of a wide range of eukaryotes.

miRNAs and other small RNA molecules have been implicated in a number of human diseases such as cancer, cardiovascular disease, viral infection and metabolic disorders. Accordingly, it is critical that specific and sensitive analytical methods are available for detecting when, where and at what levels small RNAs are expressed (whether up or down regulated), in order to realize the full diagnostic and therapeutic potential of this important new class of targets. Unfortunately, due to their small size, applying conventional nucleic acid detection methodologies, such as amplification-based techniques, to the detection of small RNAs has been problematic. Their small size offers little sequence for designing hybridization probes and primers and, in fact, most conventional PCR primers are similar in length to the miRNAs themselves.

Various approaches have been used for detecting miRNAs including Northern blots, primer extension, signal-amplifying ribozymes and some amplification-based techniques. However, these and other conventional strategies for detecting small RNAs have been associated with problems relating to specificity, sensitivity, expense and/or ease of implementation.

Therefore, there is a need in the art for versatile, simple, and inexpensive compositions, methods and kits for use in the detection of small RNA sequences, which allow for rapid and robust amplification and detection. The present invention addresses these needs and offers other related advantages.

BRIEF DESCRIPTION OF DRAWINGS

FIG. 1 shows exemplary forward and reverse primers (SEQ ID NOS: 1 and 3 respectively) designed for the detection of miR-155 (SEQ ID NO:2) by reverse transcription-polymerase chain reaction (RT-PCR).

FIG. 2 shows improved efficiency and sensitivity of detection achieved by incorporating base-modified duplex-stabilizing dNTPs in a cDNA strand prior to PCR amplification.

SUMMARY OF THE INVENTION

As noted above, the present invention relates generally to the use of base-modified, duplex-stabilizing nucleoside triphosphates in reverse transcription reactions for improving duplex stability during subsequent amplification-based detection of short RNA sequences, such as miRNA.

Therefore, according to one aspect of the invention, there is provided a method for reverse transcription of at least one RNA target sequence, such as a small RNA target sequence, which comprises: (a) contacting a sample comprising an RNA target sequence with: (i) a primer that is sufficiently complementary to the RNA target sequence to hybridize thereto, and (ii) an RNA-dependent DNA polymerase having reverse transcriptase activity; and (b) synthesizing cDNA complementary to the RNA target sequence in the presence of a mixture of dNTPs comprising at least one base-modified, duplex-stabilizing dNTP that is a substrate for the RNA-dependent DNA polymerase.

Essentially any base-modified duplex-stabilizing dNTP can be use in accordance with the present invention provided that it is a substrate for RNA-dependent DNA polymerase and provided further that it results in enhanced hybridization properties, as described herein, when incorporated into cDNA.

In some embodiments of the invention, for example, the base-modified, duplex-stabilizing dNTP is a pyrimidine substituted at the 5-position, and which is a substrate for a reverse transcriptase enzyme.

In some embodiments, the base-modified, duplex-stabilizing dNTP comprises a compound having the following structure:

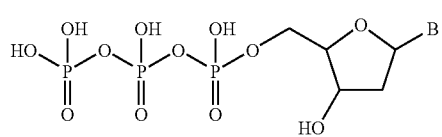

where B is selected from:

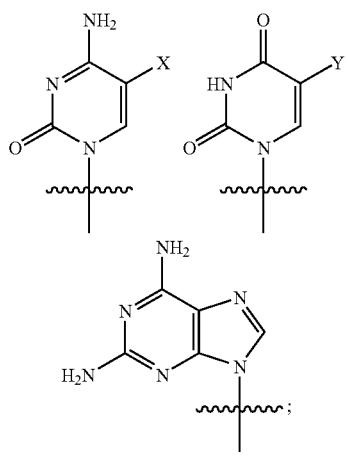

X is selected from —F, —Cl, —Br, —I, —CH₃ or

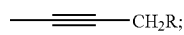

Y is selected from —F, —Cl, —Br, —I or

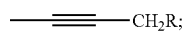

and

R is —H, —OH, —OCH₃ or —NH₂.

In some embodiments, the base-modified, duplex-stabilizing dNTP is selected from d(2-amA)TP, d(5-PrU)TP, d(5-PrC)TP, or a combination thereof.

The invention can be employed in the detection of essentially any RNA target, however, as described herein, this invention will find particular applicability in the detection of small RNA target sequences where detection by amplification-based approaches has been problematic by conventional techniques. In certain embodiments, the RNA target is a small RNA target, such as an RNA sequence about 10-30 nucleotide in length. In certain other embodiments, the small RNA target sequence is miRNA.

In addition to incorporating base-modified, duplex-stabilizing dNTPs into cDNA during reverse transcription, it will be understood that base-modified, duplex-stabilizing dNTPs may also be incorporated in the primers or other oligonucleotides used during reverse transcription and/or during subsequent amplification to further enhance their hybridization properties, and may additionally be incorporated into amplification products synthesized during amplification, if necessary or desired.

In some embodiments of the invention, the primer used in cDNA synthesis is also used as a reverse primer in a subsequent amplification reaction, whereas, in another embodiment, a different reverse primer is used.

In some embodiments of the invention, the method described above further comprises the steps of: (a) treating the cDNA formed in step (b) to provide single-stranded cDNA; and (b) contacting the single-stranded cDNA with a second primer that is sufficiently complementary to the cDNA to hybridize thereto and initiate synthesis of an extension product in the presence of a DNA polymerase to produce a double-stranded cDNA molecule.

In some embodiments, a the invention further comprises the step of performing a nucleic acid amplification reaction using amplification primers that are sufficiently complementary to the small RNA target sequence and its complement to hybridize thereto and produce amplification products in the presence of DNA polymerase. In some embodiments, the nucleic acid amplification reaction is a polymerase chain reaction. As noted above, the amplification reaction may optionally be performed in the presence of a mixture of dNTPs containing at least one base-modified duplex-stabilizing dNTP, such that the modified dNTPs are incorporated into amplification products.

According to another aspect of the present invention, there are provided reaction mixtures used in carrying out the methods of the present invention. For example, in some embodiments, a reaction mixture of the invention comprises (a) a sample comprising an RNA target sequence, such as at least one small RNA target sequence; (b) a primer that is sufficiently complementary to the RNA target sequence to hybridize therewith, (c) an RNA-dependent DNA polymerase having reverse transcriptase activity; and (d) a mixture of dNTPs containing at least one base-modified duplex-stabilizing dNTP, as described herein, which is a substrate for the RNA-dependent DNA polymerase.

According to another aspect, the invention provides kits comprising components necessary or important for practice of the present invention. For example, in some embodiments, the invention provides a kit comprising (a) an RNA-dependent DNA polymerase having reverse transcriptase activity; and (b) at least one base-modified, duplex-stabilizing dNTP, as described herein, that is a substrate for the RNA-dependent DNA polymerase. The kit may further comprise any of a number of additional components including, for example, one or more primers that specifically hybridize to one or more RNA target sequences, for use during reverse transcription and/or amplification of the RNA target sequence.

These and other features and advantages of the present invention will become apparent upon reference to the following detailed description, the attached drawings and the claims. All references disclosed herein are hereby incorporated by reference in their entirety as if each was incorporated individually.

DETAILED DESCRIPTION OF THE INVENTION

As noted above, the present invention relates generally to improved amplification and detection of RNA targets, particularly small RNA targets such as miRNA and siRNA. More specifically, the invention relates to improved methods for detecting RNA target sequences by reverse transcription of an RNA target sequence in the presence of base-modified duplex-stabilizing dNTPs under conditions where the base-modified duplex-stabilizing dNTPs are incorporated into the cDNA that is synthesized by an RNA-dependent DNA polymerase. By incorporation of base-modified duplex-stabilizing dNTPs into cDNA during reverse transcription, to produce a modified cDNA, when a polynucleotide component hybridizes to the modified cDNA during subsequent manipulations (e.g., during subsequent amplification), it forms a hybridization complex having improved stability. As a result, improvements in yield and sensitivity, for example, can be achieved during subsequent amplification reactions by practicing the methods herein. Further improvements can be realized, in accordance with the present invention, by optionally incorporating one or more base-modified duplex-stabilizing dNTPs into an amplification reaction following the reverse transcription and/or into the primers or other auxiliary oligonucleotides employed during reverse transcription and/or amplification.

In general, the aspects of the invention disclosed herein may be used to benefit virtually any assay that is based on synthesis, amplification and/or detection RNA molecules, provided that at least one oligonucleotide component (e.g., oligonucleotide primer(s) and/or probe(s)) hybridizes to modified DNA, as described herein, with greater stability than would occur if the DNA was not so modified. Those of ordinary skill in the art will further appreciate that the present invention may benefit RNA detection assays in a variety of ways, for example by expanding and simplifying the design of oligonucleotide components for amplification and/or detection, by allowing the amplification and detection of RNA sequences (e.g., small RNA sequences) which have been problematic using conventional approaches, by accelerating amplification and/or detection stages (e.g. assay time reduction), etc.

The practice of the present invention, as well as the terms and symbols of biochemistry, nucleic acid chemistry, molecular biology and molecular genetics, unless otherwise indicated, will follow those conventionally understood within the art, as more fully explained in the literature. See, e.g., *Molecular Cloning A Laboratory Manual,* 2nd Ed., Sambrook et al., ed., Cold Spring Harbor Laboratory Press: (1989); *DNA Cloning,* Volumes I and II (D. N. Glover ed., 1985); *Oligonucleotide Synthesis* (M. J. Gait ed., 1984); Mullis et al., U.S. Pat. No. 4,683,195; *Nucleic Acid Hybridization* (B. D. Hames & S. J. Higgins eds. 1984); B. Perbal, *A Practical Guide To Molecular Cloning* (1984); the treatise, *Methods In Enzymology* (Academic Press, Inc., N.Y.); Ausubel et al., *Current Protocols in Molecular Biology*, John Wiley and Sons, Baltimore, Md. (1989); Kornberg and Baker, DNA Replication, Second Edition (W.H. Freeman, New York, 1992); Gaits, ed., Oligonucleotide Synthesis: A Practical Approach (IRL Press, Oxford, 1984); Lehninger, Biochemistry, Second Edition (Worth Publishers, New York, 1975); Eckstein, ed., Oligonucleotides and Analogs: A Practical Approach (Oxford University Press, New York, 1991); and the like.

DEFINITIONS

The following terms have the meanings set forth herein unless expressly stated to the contrary. It is to be noted that the term "a" or "an" entity refers to one or more of that entity; for example, "a nucleic acid," is understood to represent one or more nucleic acids. As such, the terms "a" (or "an"), "one or more," and "at least one" can be used interchangeably herein.

The term, "sample" as used herein refers to any substance containing or presumed to contain a nucleic acid of interest, and thus includes a sample of nucleic acid, cells, organisms, tissue, fluids (e.g., spinal fluid or lymph fluids), and samples including but not limited to plasma, serum, urine, tears, stool, respiratory and genitourinary tracts, saliva, fragments of different organs, tissue, blood cells, samples of in vitro cell cultures, isolates from natural sources and objects or specimens that have been suspected to contain nucleic acid molecules. The samples may be derived from normal tissues, diseased tissues and/or tissues from subjects suspected of having a disease.

The term "polynucleotide" and "oligonucleotide" are used interchangeably herein, and each means a linear polymer of nucleotide monomers. Polynucleotides typically range in size from a few monomeric units, e.g. 5-40, when they are usually referred to as "oligonucleotides," to several thousand monomeric units. The exact size will depend on many factors, which in turn depends on the ultimate function or use of the oligonucleotide. The oligonucleotide may be generated in any manner, including chemical synthesis, DNA replication, reverse transcription, or a combination thereof. Whenever a polynucleotide or oligonucleotide is represented by a sequence of letters, for example, "CCGTATG," it is understood herein, unless otherwise specified in the text, that the nucleotides are in 5'→3' order from left to right and that "A" denotes deoxyadenosine, "C" denotes deoxycytidine, "G" denotes deoxyguanosine, and "T" denotes deoxythymidine, unless otherwise indicated or obvious from context. Usually DNA polynucleotides comprise these four deoxyribonucleosides linked by phosphodiester linkage whereas RNA comprises their four ribose counterparts with uridine ("U") in place of "T".

The term "oligonucleotide primer" or "primer" as used herein refers to a single-stranded DNA or RNA molecule that is sufficiently complementary to a target sequence to hybridize thereto and prime the enzymatic synthesis of a nucleic acid strand in presence of a DNA polymerase. The target nucleic acid serves as a template for the oligonucleotide primer. Primers are used in both reverse transcription and amplification reactions as described herein. An oligonucleotide primer may occur naturally, as in a purified restriction digest or may be produced synthetically. In particular aspects, a primer is selected to have on its 3' end a region that is substantially complementary to a strand of specific sequence of the template. A primer must be sufficiently complementary to hybridize with a template strand for primer extension to occur. An oligonucleotide primer sequence need not reflect the exact sequence of the template in order to hybridize thereto. For example, a non-complementary nucleotide fragment may be attached to the 5' end of the primer, with the remainder of the primer sequence being substantially complementary to the strand. A 5' tail sequence, for example, may incorporate a specialty fragment or combination of specialty fragments which serve a desired purpose, such as improving the efficiency, yield, detectability, etc., of reverse transcription and/or amplification reactions, or that are desired or required by the choice of amplification or detection technologies employed. For example, a 5' tail sequence may be added to improve the hybridization properties of primers used according to the methods described herein. Other examples of specialty sequences include, but are not limited to, fragments containing probe binding sites, separating sequences, target-extending sequences, anti-primer-dimer sequences, etc., as are known in the art. Further, non-complementary bases or longer sequences can be interspersed within the primer, provided that the primer sequence retains sufficient complementarity with the sequence of the template to hybridize and thereby form a template-primer complex for synthesis of the extension product of the oligonucleotide primer. Alternatively, or in addition, base-modified duplex-stabilizing dNTPs may be incorporated into one or more primers used in accordance with the present invention in order to improve their binding properties provided the presence of the base-modified duplex-stabilizing dNTPs does not prohibit hybridization to a target sequence or the ability to synthesize an extension product therefrom. In certain embodiments, relatively short primers may be advantageously used (e.g., as small as 8, 9 or 10 nucleotides) during reverse transcription and/or amplification as a result of the improved hybridization properties of such primers when modified dNTPs of the invention are incorporated therein.

The terms, "target nucleic acid" or "target sequence" or "nucleic acid of interest" refers to a nucleic acid or a fragment of nucleic that is to be reverse transcribed, amplified and/or detected using one or more methods of the present invention. In some embodiments, the target sequence is a small RNA sequence, such as miRNA or siRNA. The target nucleic acid may be derived from any organism or other source, including but not limited to prokaryotes, eukaryotes, plants, animals, and viruses, as well as synthetic nucleic acids. The target nucleic acids may contain DNA, RNA, and/or variants or derivatives thereof. Target nucleic acids can be single-stranded or double-stranded, and when a nucleic acid of interest is, or presumed to be double-stranded, the term "target nucleic acid" refers to a specific sequence in either strand of the double-stranded nucleic acid. Therefore, a full complement to any single-stranded nucleic acid of interest is treated for particular embodiments herein as the same target nucleic acid.

In some embodiments, the nucleic acids of interest may be isolated and purified from a sample source before applying methods of the present invention. Preferably, the target nucleic acids are sufficiently free of proteins and/or any other substances that interfere with reverse transcription, amplification and/or detection reactions. Many art recognized methods are available for the isolation and purification of target nucleic acids, including commercial kits and specialty instruments. For example, nucleic acids can be isolated using organic extraction with a phenol/chloroform organic reagent followed by ethanol precipitation (Ausubel et al., eds., Current Protocols in Molecular Biology Vol. 1, Chapter 2, Section I, John Wiley & Sons, New York (1993). Solid phase adsorption method (Walsh et al. (1991) *Biotechniques*, 10:506-513, Boom et al., U.S. Pat. No. 5,234,809) and salt-induced precipitation (Miller et al (1988) Nucleic Acids Res., 16:1215) are yet other known approaches to purify nucleic acids.

"Small RNA sequences" refer generally to RNA sequences having lengths from about 15-100, 15-75, 15-50, 15-30, or 15-25 nucleotides in length. In more particular embodiments, a small RNA sequence detected in accordance with the invention is about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100, or more, nucleotides, or any range bounded by any of the foregoing lengths. In certain embodiments, small RNAs refer to short non-coding RNA sequences that include micro RNAs (mi), short interfering (si) RNAs, small temporal (st) RNAs, heterochromatic siRNAs, tiny noncoding RNAs, etc. Small RNAs can function, for example in the control of mRNA stability or translation and/or can target epigenetic modifications to specific regions of the genome. As discussed above, the present invention, in certain aspects, addresses the difficulties associated with detection of these sequences via conventional amplification-based approaches due to their short lengths.

"miRNA" as used herein refers to microRNA sequences which comprise small RNA molecules encoded in the genomes of plants and animals. miRNAs are naturally occurring RNAs typically ~17-24 nucleotides in length (e.g., 17, 18, 19, 20, 21, 22, 23 of 24 nucleotides) which regulate the expression of genes, many of which have association with a human disease state or other condition. The number of miRNA sequences identified to date is large and growing, illustrative examples of which can be found, for example, in: "*miRBase: microRNA sequences, targets and gene nomenclature*" Griffiths-Jones S, Grocock R J, van Dongen S, Bateman A, Enright A J. NAR, 2006, 34, Database Issue, D140-D144; "*The microRNA Registry*" Griffiths-Jones S. NAR, 2004, 32, Database Issue, D109-D111; and also at http://microrna.sanger.ac.uk/sequences/.

"Hybridizing," "hybridization" or "annealing" as used herein refers to a process of interaction between two or more polynucleotides forming a complementary complex through base pairing which is most commonly a duplex or double-stranded complex as originally described in Marmur J., Lane D. (1960) *Proc. Natl. Acad. Sci. USA*, 46:453-461 and Doty P. et al (1960) *Proc. Natl. Acad. Sci. USA*, 46:461-476. The stability of a nucleic acid duplex can be measured by the melting temperature, or "$T_m$." The $T_m$ of a particular nucleic acid duplex under specified conditions is the temperature at which, on average, half of the base pairs have disassociated.

"Hybridization properties" of a polynucleotide refers to the ability of this polynucleotide or a fragment thereof to form a sequence-specific complex with another complementary polynucleotide or its fragment. "Hybridization properties" also generally refers herein to the complementary complex stability. In this regard, "hybridization properties" is used in a similar fashion to "melting temperature" or "Tm."

As used herein, "modified DNAs" refers to DNA incorporating at least one base-modified duplex-stabilizing nucleotide, as described herein. In certain preferred embodiments, the modified DNA is a modified cDNA produced by reverse transcription of an RNA target sequence in presence of a mixture of deoxynucleoside 5'-triphosphates (dNTPs) containing at least one base-modified duplex-stabilizing dNTP, as described herein.

The term "base-modified duplex-stabilizing dNTP" as used herein refers to a deoxynucleoside 5'-triphoshate which contains an unnatural base (base-modified) and which, when incorporated into a polymer with other dNTPs, whether natural or base-modified, in presence of a DNA polymerase, provides a modified DNA with enhanced hybridization properties (is duplex-stabilizing). A base-modified duplex-stabilizing dNTP can be an analog of the respective natural dNTP, e.g. d(5-MeC)TP (5-methyl cytosine) is an analog of dCTP (cytosine), d(2-amA)TP (2-amino adenosine, also referred to as 2,6-diamino purine) is an analog of dATP (adenosine), etc. Illustrative examples of base-modified duplex-stabilizing dNTPs are further described herein. A base-modified duplex-stabilizing dNTP can completely replace its respective natural dNTP. This means, for example, that, if d(5-MeC)TP is used in the amplification reaction, the reaction does not contain dCTP. Alternatively, a base-modified duplex-stabilizing dNTP can represent a fraction of the respective natural dNTP. This means that both natural dNTP and its analog are present in the reaction mixture, and typically where the base-modified duplex-stabilizing dNTP represents, at least a certain proportion (e.g., 5%, 25%, 50% or 75%), of the molar amount of the respective natural dNTP. A primer or cDNA or amplicon used or synthesized in accordance with the invention may thus comprise any suitable or desired number of base-modified, duplex stabilizing dNTPs incorporated therein (e.g., 1, 2, 3, 4, 5, 6, 7, 8, 9, 10, 11, 12, 13, 14, 15, 25, 50, 75, 100, etc., and all integers in between).

As used herein the phrase "reverse transcription" refers to a process whereby an RNA-dependent DNA polymerase having reverse transcriptase activity extends an oligonucleotide primer hybridized to an RNA template, in the presence of deoxynucleoside 5'-triphosphates (dNTPs), whether natural or modified, resulting in synthesis of complementary DNA (cDNA).

An "RNA-dependent DNA polymerase" or "reverse transcriptase" ("RT") is an enzyme that synthesizes a complementary DNA copy from an RNA template in a process referred to as reverse transcription. A primer is required to initiate synthesis with both RNA and DNA templates.

By "amplification" or "nucleic acid amplification" is meant production of multiple copies of a target nucleic acid that contains at least a portion of the intended specific target nucleic acid sequence. The multiple copies may be referred to as amplicons or amplification products. Typically, the amplified portion contains a detectable target sequence that may be detected using any of a variety of well-known methods. One of the most common nucleic acid amplification techniques, polymerase chain reaction (PCR), requires thermocycling to alternately denature double-stranded nucleic acids and hybridize primers; however, other well-known methods of nucleic acid amplification are isothermal. The polymerase chain reaction (Mullis et al., U.S. Pat. No. 4,683,195; Mullis, U.S. Pat. No. 4,683,202; and Mullis et al., U.S. Pat. No. 4,800,159), commonly referred to as PCR, uses multiple cycles of denaturation, annealing of primer pairs to opposite strands, and primer extension to exponentially increase copy numbers of the target sequence. Many other nucleic acid amplification techniques have also been described, as discussed further herein, and can be applied in the context of the present invention.

As used herein "reverse transcription-polymerase chain reaction" or "RT-PCR" refers to the well known technique for amplification and detection of a target RNA sequence wherein an RNA-dependent DNA polymerase having reverse transcriptase (RT) activity is used to make a complementary DNA (cDNA) from an RNA target sequence, and the cDNA is then amplified by PCR to produce multiple copies of DNA (e.g., Gelfand et al., "Reverse Transcription with Thermostable DNA Polymerases-High Temperature Reverse Transcription," U.S. Pat. Nos. 5,322,770 and 5,310,652).

By "detectable amplification" is meant that a detectable signal associated with an amplification product in an amplification reaction mixture rises above a predetermined background or threshold level (end-point amplification) or rises above a background or threshold level within a certain period of time (real-time amplification). See, e.g., Light et al., "Method for Determining the Amount of an Analyte in a Sample," U.S. Pat. Appln. Pub. No. US 2006-0276972, paragraphs 506-549. The amplification product contains a sequence having sequence identity with a target nucleic acid sequence or its complement and can be detected with, for example, an intercalating dye or a detection probe having specificity for a region of the target nucleic acid sequence or its complement.

By "amplification conditions" is meant conditions permitting nucleic acid amplification. Oligonucleotides used in the reverse transcription and/or amplification reactions of the present invention hybridize to their intended targets under amplification conditions, but may or may not hybridize under stringent hybridization conditions. While the Examples section infra provides illustrative amplification conditions for reverse transcription and amplification of target nucleic acid sequences according to the present invention, it will be understood that other acceptable conditions may also be used and such conditions can be easily ascertained by a person having ordinary skill in the art depending on the particular sequence being detected and/or method of amplification employed.

The term "oligonucleotide component" refers to any oligonucleotide or polynucleotide that is required or useful in conducting reverse transcription, amplification and/or detection reactions of the invention. Oligonucleotide components include but not limited to oligonucleotide primers, probes, hybridization and cleavage enhancers, effectors, etc. Oligonucleotide components can be labeled or have structural modifications including those used in oligonucleotide primer and probe designs.

As used herein, the term an "oligonucleotide probe" refers to an oligomer or polymer used in detecting a target nucleic acid that forms a duplex structure or other complex with the target nucleic acid, based on complementarity of at least one sequence in the probe with a sequence in the target nucleic acid. Oligonucleotide primers and probes of the present invention can be "modified" or contain "structural modifications."

"Duplex-stabilizing modifications" refer to structural modifications, which when present in nucleic acids provide duplex-stabilizing effects when compared in terms of thermal stability, usually measured as Tm, with the respective nucleic acid complexes that have no structural modification, e.g. comprising of natural nucleotides.

The term "natural nucleosides" as used herein refers to four deoxynucleosides which may be commonly found in DNAs isolated from natural sources. Natural nucleosides are deoxyadenosine, deoxycytidine, deoxyguanosine, and deoxythymidine. The term also encompasses their ribose counterparts, with uridine in place of thymidine.

As used herein, the term "unnatural nucleosides" refers to nucleoside analogs that are different in their structure from those natural nucleosides for DNA and RNA polymers. Some of the naturally occurring nucleic acids of interest may contain nucleosides that are structurally different from the natural nucleosides defined above, for example, DNAs of eukaryotes may incorporate 5-methyl-cytosine and tRNAs harbor certain nucleoside analogs. However, as used herein in particular aspects, the term "unnatural nucleosides" nonetheless encompasses these nucleoside modifications even though they can be found in natural sources. For example, ribothymidine is treated herein as an unnatural nucleoside.

"Improved" or "enhanced hybridization properties" of a polynucleotide, as used herein, refers to the enhanced hybridization properties resulting from practice of the present invention. For example, use of base-modified duplex-stabilizing dNTPs in assays of the present invention leads to the synthesis of a modified cDNA wherein this modified cDNA is said to have enhanced hybridization properties. This means that the thermal stability or Tm of a complementary complex of this modified DNA with, for example, oligonucleotide probes or primers, is greater than that of a DNA comprising respective natural bases.

"Melting temperature" or "Tm" refers to the temperature at which a complementary complex of nucleic acids, usually double-stranded, becomes half dissociated into single strands. These terms are also used in describing stabilities of polynucleotide secondary structures wherein two or more fragments of the same polynucleotide interact in a complementary fashion with each other forming complexes, e.g., hairpin-like structures, etc. A simple estimate of the Tm value may be calculated using the equation Tm=81.5+0.41(% G+C), when a nucleic acid is in aqueous solution at 1 M NaCl. More accurate calculations can be made using the base pair thermodynamics of a "nearest-neighbors" approach (Breslauer K. J. et al (1986) *Proc. Natl. Acad. Sci. USA*, 83:3746-3750; SantaLucia J. Jr. (1998) *Proc. Natl. Acad. Sci. USA*, 95:1460-1465).

The term "label" refers to any atom or molecule that can be used to provide a detectable signal and that can be attached to a nucleic acid or oligonucleotide. Labels include but are not limited to isotopes, radiolabels such as $^{32}P$; binding moieties such as biotin; haptens such as dioxygenin; luminogenic, mass tags; phosphorescent or fluorescent moieties, fluorescent dyes alone or in combination with other dyes or moieties that can suppress or shift emission spectra by FRET effect. Labels may provide signals detectable by fluorescence, radioactivity, colorimetry, gravimetry, X-ray diffraction or absorption, magnetism, enzymatic activity, mass spectrometry, binding affinity and the like. A label may be a charged moiety or alternatively, may be charge neutral. Labels can include or consist of nucleic acid or protein sequence, so long as the sequence comprising the label is detectable.

A "reaction mixture" generally refers to a solution containing the necessary reactants for performing a reverse transcription reaction, amplification reaction and/or detection reaction, which in addition to main components such as target nucleic acids, DNA polymerases, oligonucleotide primers, probes or other oligonucleotide components, may also optionally include detecting agents, specialty enzymes, nucleoside 5'-triphosphates including the modified ones, buffering agents to maintain pH at a selected level during a reaction, salts, co-factors and additives, for example, 1-methyl-2-pyrrolidinone, glycerol, poly(ethylene glycol), dimethyl sulfoxide or formamide, and the like.

As used herein, the term "kit" refers to any system for delivering materials. In the context of reaction assays, such delivery systems include elements allowing the storage, transport and/or delivery of reaction components such as oligonucleotides, buffering components, additives, reaction enhancers, enzymes and the like in the appropriate containers from one location to another commonly provided with written instructions for performing the assay. Kits may include one or more enclosures or boxes containing the relevant reaction reagents and supporting materials. The kit may comprise two or more separate containers wherein each of those containers includes a portion of the total kit components. The containers may be delivered to the intended recipient together or separately.

Reverse Transcription-Mediated Synthesis of Modified cDNA

As noted above, an important aspect of the present invention relates to the synthesis of modified cDNA by reverse transcription of an RNA target sequence. Reverse transcription is a well known process whereby an RNA-dependent DNA polymerase enzyme having reverse transcriptase activity catalyzes the template dependent synthesis of complementary DNA (cDNA). An RNA target sequence of interest can be converted in a reverse transcription reaction to cDNA/RNA heteroduplexes or to duplex cDNA, for example as described in Simpson D. et al (1988) *Biochem. Biophys. Res. Commun.*, 151: 487-492; Belyavsky A. et al (1989) *Nucleic Acids Res.*, 17: 2919-2932, and many other references. These methods rely upon reverse transcriptases extending an oligonucleotide primer hybridized to an RNA template in the presence of deoxynucleoside 5'-triphosphates (dNTPs).

It has been found, in accordance with the present invention, that reverse transcriptase enzymes can adopt and use as substrates base-modified duplex-stabilizing dNTPs and, furthermore, that incorporation of such base-modified duplex-stabilizing dNTPs into cDNA during reverse transcription provides improved hybridization properties and, as a result, improved efficiency and sensitivity in subsequent amplification-based detection of target sequences. Thus, in accordance with the present invention, improved methods are provided for the amplification-based detection of RNA sequences, particularly small RNA sequences (e.g., miRNA or siRNA), by synthesizing modified cDNAs which contain base-modified duplex-stabilizing dNTPs.

Modified cDNAs of the invention having enhanced hybridization properties are produced by carrying out reverse transcription reactions in the presence of a DNA polymerase having reverse transcriptase activity (e.g., a reverse transcriptase) and a mixture of dNTPs which comprises at least one and often more than one base-modified duplex-stabilizing dNTP. A reverse transcription reaction of the invention can include all four natural dNTPs (dTTP, dCTP, dATP and dGTP) provided that one or more of the natural dNTPs is partially or completely substituted with a respective base-modified duplex-stabilizing dNTP.

Base-modified duplex-stabilizing dNTPs useful in the methods herein include, but are not limited to, dNTP analogs that act as substrates for a DNA polymerase enzyme having reverse transcriptase activity and which catalyze the synthesis of a cDNA sequence having enhanced duplex stability as a result of incorporation of the dNTP analogs therein.

Certain illustrative base-modified duplex-stabilizing dNTPs of the present invention contain 2-deoxy-D-ribose wherein the nucleotide base is modified. Such nucleoside analogs can be synthesized applying well known techniques of organic chemistry which are exemplified in e.g. Townsend L. B., ed. (1988) Chemistry of Nucleosides and Nucleotides, Plenum Press, NY. Respective 5'-triphosphates can be obtained using protocols described in e.g. Vaghefi M., ed. (2005) Nucleoside Triphosphates and their Analogs: Chemistry, Biochemistry, and Biological Applications, Taylor & Francis. The base-modified duplex-stabilizing dNTPs of the present invention include certain dNTPs which can be obtained from commercial sources, for example, Trilink (California, USA).

Other illustrative base-modified duplex-stabilizing dNTPs used in the invention include, for example, pyrimidines which are substituted at the 5-position and which are substrates for a reverse transcriptase enzyme.

In other embodiments, a base-modified duplex-stabilizing dNTPs used in the invention has the formula:

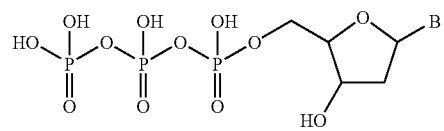

where B is selected from:

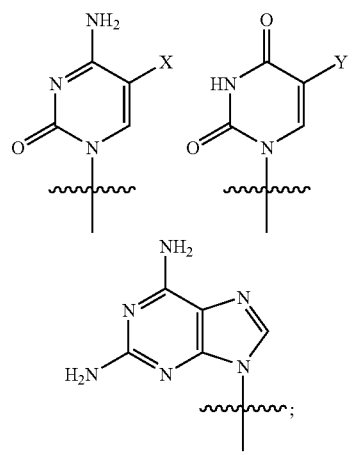

X is selected from —F, —Cl, —Br, —I, —CH₃ or

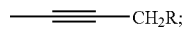

Y is selected from —F, —Cl, —Br, —I or

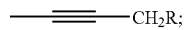

and

R is —H, —OH, —OCH₃ or —NH₂.

In a more particular embodiment, a base-modified, duplex-stabilizing dNTP used in the methods herein is selected from d(2-amA)TP, d(5-PrU)TP, d(5-PrC)TP, or a combination thereof.

Those of ordinary skill in the art will appreciate that certain adjustments or variations of the methods can be applied in the use of the base-modified duplex-stabilizing dNTPs, depending on the nature of a particular amplification reaction, particularly those comprising enzymes other than DNA polymerase (restriction endonucleases, RNA polymerases, etc.). The base-modified duplex-stabilizing dNTPs will preferably not interfere with other enzymatic activities where they are key components of the reaction or DNA synthesis. This may dictate the choice of the base-modified duplex-stabilizing dNTPs to be used in a particular amplification schemes and the choice may be made based on the properties of these enzymes, which are well known in the art.

Nucleic Acid Amplification of Modified cDNA

Modified cDNA synthesized as described above can interact with at least one and preferably more than one oligonucleotide primer or probe during subsequent manipulations (e.g., amplification reactions) to form hybridization complexes having enhanced stability by virtue of the modified cDNA of the invention having enhanced hybridization properties compared to a cDNA that has not been modified with duplex-stabilizing base analogs. As a result, the primers or probes that hybridize to the modified cDNA during subsequent amplification reactions, for example, provides improved sensitivity, efficiency, yield, etc., as a result of their enhanced hybridization properties.

Therefore, according to another aspect of the invention, following reverse transcription of a target sequence to produce a modified cDNA, as described above, a nucleic acid amplification reaction is performed in order to increase the copy number of the target sequence. In one preferred embodiment, amplification of the target nucleic acids is accomplished using the "polymerase chain reaction" ("PCR") (Mullis K. B. et al, U.S. Pat. No. 4,683,195; Mullis K. B., U.S. Pat. No. 4,683,202). The most commonly used PCR profile employs two oligonucleotide primers, one for each strand, which are designed so that the extension of one primer provides a template for the other primer in the next PCR cycle. Generally, a PCR consists of repetition (or cycles) of (i) a denaturation step that separates the strands of a double-stranded nucleic acid comprising a target sequence, followed by (ii) an annealing step that allows primers to anneal to positions flanking the target sequence; and (iii) an extension step that extends the primers in a 5' to 3' direction, thereby forming an 'amplicon' nucleic acid having sequences complementary to the target sequence. Each of the above three steps may be conducted at a different temperature using an automated thermocycler. The PCR cycles can be repeated as many times as desired, resulting, at least in theory, in an exponential accumulation of a target DNA fragment whose termini are defined by the 5' ends of the primers used. Particular temperatures, incubation times at each step, and rates of change between steps depend on many factors well-known to those of ordinary skill in the relevant art, and relevant examples can be found in numerous published protocols; for example, McPherson M. J. et al. (1991 and 1995) and the like. Although conditions of PCR can vary over a broad range, in a conventional PCR, a double-stranded target nucleic acid is generally denatured at temperature >90° C., primers are annealed at a temperature in the range 50-75° C., and the extension is generally performed in the range 72-78° C. It is also well known that PCR reactions can be performed wherein annealing and extension are combined in a single step.

Additional guidance for performing the PCR reactions can be found, for example, in Clementi M. et al (1993) *PCR Methods Appl.*, 2: 191-196; Clegg R. M. (1992) *Methods Enzymol.*, 211:353-388; Clementi M. et al (1993) *PCR Methods Appl.*, 2: 191-196; Lie Y. S. and Petropoulos C. J. (1998) *Curr. Opin. Biotech.*, 9: 43-48; Livak K. J. et al (1995) *PCR Methods and Applications*, 4: 357-362; McPherson M. J. et al, eds (1991) *PCR: A Practical Approach*. IRL Press, Oxford; McPherson M. J. et al, eds (1995) *PCR2: A Practical Approach*. IRL Press, Oxford, and many other manuscripts referred herein.

There are numerous nucleic acid amplification techniques, in addition to PCR, which are known and available in the art, many of which can be readily applied for use in accordance with the present invention.

One amplification method is strand displacement amplification (Walker, G. et al. (1992), *Proc. Natl. Acad. Sci. USA* 89, 392-396; Walker et al., "Nucleic Acid Target Generation," U.S. Pat. No. 5,270,184; Walker, "Strand Displacement Amplification," U.S. Pat. No. 5,455,166; and Walker et al. (1992) *Nucleic Acids Research* 20, 1691-1696), commonly referred to as SDA, which uses cycles of annealing pairs of primer sequences to opposite strands of a target sequence, primer extension in the presence of a dNTP to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (European Pat. No. 0 684 315).

Other illustrative amplification methods include: nucleic acid sequence based amplification (Malek et al., U.S. Pat. No. 5,130,238), commonly referred to as NASBA; one that uses an RNA replicase to amplify the probe molecule itself (Lizardi, P. et al. (1988) *BioTechnol.* 6, 1197-1202), commonly referred to as Qβ replicase; a transcription-based amplification method (Kwoh, D. et al. (1989) *Proc. Natl. Acad. Sci. USA* 86, 1173-1177); self-sustained sequence replication (Guatelli, J. et al. (1990) *Proc. Natl. Acad. Sci. USA* 87, 1874-1878; Landegren (1993) *Trends in Genetics* 9, 199-202; and Lee, H. et al., NUCLEIC ACID AMPLIFICATION TECHNOLOGIES (1997)); and, transcription-mediated amplification (Kacian et al., "Nucleic Acid Sequence Amplification Methods," U.S. Pat. No. 5,480,784; and Kacian et al., U.S. Pat. No. 5,399,491), commonly referred to as TMA. For further discussion of known amplification methods see Persing, David H., 1993, "In Vitro Nucleic Acid Amplification Techniques" in Diagnostic Medical Microbiology: Principles and Applications (Persing et al., Eds.), pp. 51-87 (American Society for Microbiology, Washington, D.C.). Still other illustrative amplification methods include rolling circle amplification (RCA) (Lizardi, "Rolling Circle Replication Reporter Systems," U.S. Pat. No. 5,854,033); Helicase Dependent Amplification (HDA) (Kong et al., "Helicase Dependent Amplification Nucleic Acids," U.S. Pat. Appln. Pub. No. US 2004-0058378 A1); and Loop-Mediated Isothermal Amplification (LAMP) (Notomi et al., "Process for Synthesizing Nucleic Acid," U.S. Pat. No. 6,410,278).

DNA polymerases are obviously key components in practicing nucleic acid amplification of the present invention. DNA polymerases useful according to the invention include both native polymerases as well as polymerase mutants, which lack 5' to 3' and/or 3' to 5' exonuclease activity. Nucleic acid polymerases can possess different degrees of thermostability. The choice of DNA polymerase is determined by many factors that usually relate to the choice of the amplification and detection reactions applied in the invention. In certain embodiments, a DNA polymerase preferably exhibits strand displacement activity at the temperature at which it can extend an oligonucleotide primer. In many cases of isothermal amplification wherein DNA amplification is based on displacement of one of the DNA strand, for example, in SDA and Rolling Circle amplifications, a DNA polymerase preferably lacks 5' to 3' exonuclease activity. DNA polymerases can be isolated from various natural sources including bacteriophage, archaeal, eubacterial and eukaryotic enzymes.

Commercially-available enzymes that lack both 5' to 3' and 3' to 5' exonuclease activities include Sequenase (exo-T7; USB), Pfu exo-(Stratagene), exo-Vent (New England BioLabs), exo-DeepVent (New England BioLabs), exo-Klenow fragment (Stratagene), Bst (Bio-Rad), Isotherm (Epicentre), Stoffel fragment (Perkin-Elmer), ThermoSequenase (USB), and TaqFS (Hoffman-LaRoche). Examples of thermostable DNA polymerases which are useful for detection PCR assays include but not limited to Pfu, Taq, Vent, Deep Vent and UlTma DNA polymerases and other polymerase from Thermus species or from *Thermotoga maritima*. The thermostable polymerases for the detection PCR preferably mountain activity at temperature >90° C. and more preferably at >100° C. Certain detection reactions, for example, TaqMan assays, require use of DNA polymerase that express 5' to 3' exonuclease activity. JumpStart DNA polymerase from Sigma was used in Examples provided herein.

Depending on the choice of the DNA amplification reaction, the reaction components of the invention may vary. In addition to the main components, the reactions and reaction mixtures of the invention may include, but not be limited to, detecting agents, specialty enzymes (e.g. nucleases, FEN endonucleases, restriction endonucleases, RNAses, including RNAse H, RNA polymerases, helicases, etc.), buffering agents to maintain pH at a selected level during a reaction, salts, co-factors and additives, for example, 1-methyl-2-pyrrolidinone, glycerol, poly(ethylene glycol), dimethyl sulfoxide (DMSO) or formamide and the like.

Oligonucleotide primers initiate synthesis and amplification of modified cDNAs in the amplification reactions of the present invention. The oligonucleotide primers may occur naturally, as in a purified restriction digest or may be produced synthetically. Oligonucleotide primers of the invention must be sufficiently complementary to hybridize with a template strand for primer elongation to occur in presence of a DNA polymerase. The sequence of the oligonucleotide primers need not reflect the exact sequence of the target nucleic acids they are design to hybridize provided they are sufficiently complementary to hybridize thereto and participate in primer extension. For example, a non-complementary nucleotide fragment may be attached to the 5' end of the primer, with the remainder of the primer sequence being substantially complementary to the strand. Non-complementary bases or longer sequences can be interspersed within the primer, provided that the primer sequence has sufficient complementarity with the sequence of the template to hybridize and thereby form a template-primer complex for synthesis of the extension product of the oligonucleotide primer. Primer design can be guided by the particular amplification reaction being used. For example, the primers designed for SDA amplification incorporates a sequence of a restriction endonuclease which supports the amplification reaction, e.g. Walker G. T. et al, U.S. Pat. No. 5,270,184; Dattagupta N. et al, U.S. Pat. No. 6,214,587; Walker G. T. et al (1996) *Nucleic Acids Res.*, 24:384-353; Walker G. T. et al (1992) *Proc. Natl. Acad. Sci. USA*, 89:392-396; Spargo C. A. et al (1996) *Molecular and Cellular Probes*, 10:247-256.

Oligonucleotide primers may contain structural modifications such as atoms, moieties, residues, polymers, linkers which are usually of a synthetic nature and which are not commonly present in natural nucleic acids. The oligonucleotide primers may incorporate a detectable label, for example, isotopes, radiolabels such as $^{32}P$, binding moieties such as biotin, haptens such as dioxygenin, luminogenic, mass tags, phosphorescent or fluorescent moieties, fluorescent dyes and the like. Since primers are usually incorporated during the DNA amplification, the label may be used to detect the modified DNAs in the present invention. Oligonucleotide primers also may incorporate nucleoside or nucleotide analogs which rarely present in natural nucleic acid including but not limited to inosine (hypoxanthine), 5-bromouracil, 5-methylcytosine, 5-iodouracil, 2-aminoadenosine, 6-methyladenosine, preudouridine and the like.

In certain embodiments, oligonucleotide primers incorporate structural modifications which provide duplex-stabilizing effects. However, in all aspects of the invention, the 3' end of the primers must not be blocked in a manner that prevents the initiation of DNA synthesis. Examples of structural modifications that may be used in design of the oligonucleotide primers include, but are not limited to minor groove binders (MGB) (Afonina I. et al (1997) *Nucleic Acids Res.*, 25: 2657-2660) which are usually coupled to the 5' end and certain nucleotide analogs. Examples of the nucleotide analogs include "universal" bases (Burgner D. et al (2004) *Nucleosides Nucleotides Nucleic Acids*, 23: 755-765) and "locked nucleic acids" ("LNA") (Latorra D. et al (2003) *Mol. Cell. Probes*, 17: 253-259; Latorra D. et al (2003) *Hum. Mutat.*, 22:79-85; Di Giusto D. A. and King G. C. (2004) *Nucleic Acids Res.*, 32: e32). A number of the base-modified nucleotide analogs are well tolerated by DNA polymerases and these analogs can be used in primer design. Examples of such base-modified nucleotide analogs include but not limited to 5-methyl cytosine and 2,6-diaminopurine (Lebedev Y. et al (1996) *Genet. Anal.*, 13, 15-21).

Oligonucleotide primers can be labeled and they can be used to amplify a labeled modified DNA. The label is used in nucleic acid detection stage. A preferred label is a fluorescent label. In one aspect, an oligonucleotide primer may be coupled with an oligonucleotide probe, e.g. Scorpion primer (Whitcombe D. et al (1999) *Nature Biotech.*, 17:804-807; Thelwell N. et al (2000) *Nucleic Acids Res.*, 28:3752-3761).

Oligonucleotide probes are oligomers or polymers capable of forming duplex structures or other complexes with products of reverse transcription and/or amplification, due to complementarity of at least one sequence in the probes with respective sequences in modified DNAs. Oligonucleotide probes of the present invention can be modified or contain structural modifications. Certain modifications are commonly present in oligonucleotide probes and these usually relate to labels used in DNA detection. Fluorescently labeled oligonucleotide and, in particular, FRET probes are useful detecting components. When oligonucleotide probes and primers hybridizes to a modified DNA of the invention, they form stabilized complementary complexes because of the enhanced hybridization properties of the modified DNA. Unlike oligonucleotide primers, oligonucleotide probes have few limits in terms of structural modifications. This is especially true for the hybridization-triggered FRET probe technologies. For example, the oligonucleotide probes can be completely made of unnatural PNA monomers, e.g. Ortiz E. et al (1998) *Mol. Cell. Probes,* 12:219-226. Use of the other base-modified or sugar-modified nucleotide analogs in probe designs like LNA is also broadly applicable (Johnson M. P. et al (2004) *Nucleic Acids Res.,* 32:e55; Simeonov A. and Nikiforov T. T. (2002) *Nucleic Acids Res.,* 30:e91). Oligonucleotide probes can carry an MGB moiety conjugated to either end. For example, 5'-MGB-conjugated FRET probes are not cleaved in detection PCR and these probes provide signal due to a hybridization-triggered mechanism of action as described in Vermeulen N. et al (2002) *J. Clin. Ligand Assay,* 25: 268-275. 3'-MGB-conjugated FRET probes are not blocked from 5'-nuclease degradation and these probes generate fluorescent signal due to the cleavage by Taq polymerase, as exemplified in Kutyavin I. V. et al (2000) *Nucleic Acids Res.,* 28:655-661.

Oligonucleotide primers and probes may be synthesized using techniques that are well known in the art. Although the primers can be prepared by, for example, cloning and restriction digest analysis of appropriate sequences, direct chemical synthesis is a preferred approach. Oligonucleotides can be prepared by a suitable chemical synthesis method, including, for example, the phosphodiester method disclosed in Brown E. L. et al (1979) *Methods Enzymol.,* 68: 109-151, or the phosphotriester method described in Narang S. A. et al (1979) *Methods Enzymol.,* 68: 90-98. Another approach is the diethylphosphoramidate method disclosed in Beaucage S. L., Caruthers M. H. (1981) *Tetrahedron Lett.,* 22: 1859-1862, which can be used in combination with the solid support method disclosed in Caruthers M. H., Matteucci M. D. (1984) U.S. Pat. No. 4,458,066 and performed using one of commercial automated oligonucleotide synthesizer.

Oligonucleotide primers and probes are generally designed according to rules and specifications of a particular amplification or detection technology known in the art, including those techniques discussed and cited above. There are certain common requirements for the oligonucleotide components, for example, the hybridization properties of the oligonucleotide need to address the temperature of a particular reaction, usually referred as melting temperature (Tm). Tm defines a temperature at which a complementary complex of an oligonucleotide component with target nucleic acid becomes half dissociated into single strands. A simple estimate of the Tm value may be calculated using the equation Tm=81.5+0.41(% G+C), when a nucleic acid is in aqueous solution at 1 M NaCl. More accurate calculations can be made using the base pair thermodynamics of a "nearest-neighbors" approach (Breslauer K. J. et al (1986) *Proc. Natl. Acad. Sci. USA,* 83: 3746-3750; SantaLucia J. Jr. (1998) *Proc. Natl. Acad. Sci. USA,* 95: 1460-1465). Commercial programs, including Oligo™, Primer Design and programs available on the internet, including Primer3 and Oligo Calculator can be also used to calculate a Tm of a nucleic acid sequence useful according to the invention. Commercial programs, e.g. Visual OMP (DNA software), Beacon designer 7.00 (Premier Biosoft International), may be used in design of real time assays with SYBR Green, TaqMan and molecular beacons detection system for PCR-based and NASBA amplification reactions. In general, Tm values of the oligonucleotide probes are 5-7° C. higher than the Tm of the corresponding amplification primers.

Further, as required by certain amplification schemes, a reaction mixture of the invention may also incorporate dNTP analogs other than base-modified duplex-stabilizing dNTPs. For example, SDA amplification, described in Walker G. T. et al (1993) U.S. Pat. No. 5,270,184, requires use of a α-thio dNTP analog to promote nicking of one strand of double-stranded DNAs. Deoxyuridine 5'-triphosphate (dUTP) is yet another example. Although this base modification is known to destabilize DNA duplexes, selective use of such modified DNAs is still within the scope of the present invention. The main purpose of dUTP here is for preventing contamination carryovers from sample to sample, as described in Gelfand D. H. et al (1995) U.S. Pat. No. 5,418,149.

Detection of Amplification Products

Amplified DNA of the invention can be detected by any physical, chemical or biological means including, but not limited to, electrical force (e.g. electrophoresis), gravity (e.g. sedimentation), spectroscopy (e.g. radio spectroscopy, UV, mass spectroscopy, fluorescence, chemiluminescence, chemifluorescence, etc.), absorption, magnetism, chromatography (HPLC, reverse-phase, ion-exchange, volume exclusion, etc.), reactions with proteins (restrictases, endonucleases, polymerases, kinases and other enzymatic activities), binding affinity and the like. In certain embodiments, amplification products are labeled during or shortly after the amplification stage and the label is used in detecting the amplification products. Illustrative labels include but are not limited to isotopes, radiolabels such as $^{32}P$, binding moieties such as biotin, luminogenic and mass tags, phosphorescent or fluorescent moieties, and fluorescent dyes alone or in combination with other dyes or moieties that can suppress or shift emission spectra by a FRET effect.

In other embodiments, amplification products may be detected using a detecting agent during the amplification reaction (real time) or after. Certain preferred detecting agents are intercalating dyes and fluorescent agents, e.g. ethidium bromide. For example, amplification products in PCR can be detected using intercalating dyes as described by Wittwer C. T. et al in U.S. Pat. Nos. 6,174,670 and 6,569,627, and in Higuchi R. et al (1992) *Biotechnology,* 10:413-417; Higuchi R. et al (1993) *Biotechnology,* 11:1026-1030. Certain illustrative fluorescent agents include molecules that change their fluorescence properties upon the interaction with nucleic acids, thereby providing detectable signal. SYBR Green I and II from Invitrogen are examples of such fluorescent agents, as described in Schneeberger C. et al (1995) *PCR Methods Appl.,* 4: 234-238 and Mackay J., Landt O. (2007) *Methods Mol. Biol.,* 353: 237-262.

In certain aspects, detection of amplification products is performed in "real time." Real time detection is possible when all detection components are available during the target amplification, and the reaction conditions (e.g., temperature, buffering agents, salts, co-factors, scavengers, and the like) support both stages of the reaction-amplification and detection, thereby permitting a target nucleic acid to be measured as the amplification reaction progresses, decreasing the number of subsequent handling steps required for the detection of amplified material. Therefore, the term "Real-time PCR" as used herein refers to PCR in which the amount of reaction product, e.g., amplified target nucleic acid, is monitored as the reaction proceeds. Real-time PCR differs primarily in the detecting chemistries for monitoring the target nucleic amplification in the reaction, for example: Gelfand et al, in U.S. Pat. No. 5,210,015, describe use of 5'-nuclease cleavable FRET probes ("TaqMan"); Tyagi et al, in U.S. Pat. No. 5,925,517 describe the use of hybridization-triggered FRET probes ("Beacons"). Reviews of detection chemistries for real time PCR can be also found in Didenko V. V. (2001) *BioTechniques*, 31: 1106-1121; Mackay I. M. et al (2002) *Nucleic Acids Res.*, 30 1292-1305, and Mackay J., Landt O. (2007) *Methods Mol. Biol.*, 353 237-262.

Amplification products can also be detected using oligonucleotide probes. Oligonucleotide probes interact with DNA in a sequence-specific fashion forming a complex (e.g. complementary duplex) and this complex may be made to be more stable by virtue of the methods herein, if desired. In general, stability of the complex determines the sensitivity of the detection. Therefore, stabilization of the complex between oligonucleotide probe and modified DNA may benefit the detection assay in a variety of ways.

In another embodiment, the oligonucleotide probe incorporates a label wherein this label is used in detecting of modified DNA of the invention. In one embodiment, this label is a fluorescent label and it is used in detecting the modified DNA by a fluorescence polarization technique. In another embodiment, the oligonucleotide probe is a FRET probe. Application of FRET probes in the detection of modified DNAs, for example, can provide advantages in performing the detection assay in real time and measuring amount of target nucleic acid in the sample. When the amplification reaction is PCR, this type of the assay is termed "quantitative PCR." The FRET probe commonly contains two chromophores. The 'acceptor' chromophore may be a non-fluorescent dye chosen to quench fluorescence of the 'reporting' fluorophore (Eftink M. R. (1991) In Lakowicz J. R. (ed.), *Topics in Fluorescence Spectroscopy*. Plenum Press, New York, V.2:53-126). Formation of sequence-specific hybrids between target nucleic acid and probes leads to a change in fluorescent properties of the probe providing detection of the nucleic acid target. The real time FRET-based assays are well suited, in particular, for clinical diagnostics. Unlike intercalating dyes and fluorescent agents (e.g. ethidium bromide, SYBR Green), this detection is sequence-specific, virtually eliminating false positive results.

Many detection strategies exploiting the FRET effect have been reported. One FRET strategy is a hybridization-triggered FRET probe approach, which is based on distance change between the donor and acceptor dyes as result of a sequence-specific complex formation between a target nucleic acid and a fluorescent oligonucleotide probe. For example, the Adjacent Hybridization Probe method utilizes two oligonucleotide probes hybridizing to adjacent target DNA sequences as described in e.g. Eftink M. R. (1991) In Lakowicz J. R. (ed.), *Topics in Fluorescence Spectroscopy*. Plenum Press, New York, V.2:53-126; Heller M. J. and Morrison L. E. (1985) In Kingsbury, D. T. and Falkow, S. (eds.), *Rapid Detection and Identification of Infectious Agents*. Academic Press, New York, 245-256; Cardullo R. A. et al (1988) *Proc. Natl. Acad. Sci. USA*, 85:8790-8794. Each of the probes is labeled with FRET-pair dyes at appropriate probe ends so that when both probes are hybridized to a target DNA the donor and acceptor fluorophores are brought in sufficient spatial proximity to allow for detectable FRET.

An alternative approach utilizes quenched fluorescent probes that are cleared during PCR (e.g. U.S. Pat. No. 5,804,375). These probes include fluorescent reporter and quencher moieties conjugated to the same probe. Due to random oligonucleotide coiling, the quencher moiety is sufficiently close to the reporter dye to quench its fluorescence. Once the probe is hybridized to a complementary polynucleotide target, the quencher and reporter moieties are separated, thus enabling the reporter dye to fluoresce. Background problems often associated with this approach can be resolved by synthesizing the oligonucleotide with a flexible PNA backbone, e.g. Ortiz E. et al (1998) *Mol. Cell. Probes*, 12: 219-226.

Alternatively, efficient FRET detection can be achieved using Molecular Beacons, hairpin-shaped oligonucleotide probes in which the FRET dyes are brought in close proximity by intramolecular stem formation, e.g. Tyagi S, and Kramer F. R. (1996) *Nat. Biotechnol.*, 14: 303-308; Bonnet G. et al (1999) *Proc. Natl. Acad. Sci. USA*, 96: 6171-6176; Tyagi S. et al (2000) *Nat. Biotechnol.*, 18: 1191-1196; Marras S. A. E. et al (2002) *Nucleic Acids Res.*, 30: e122. Molecular beacon methodologies have remarkably low fluorescence background. These probes are well adapted for use in real-time PCR as described in, e.g. Piatek A. S. et al (1998) *Nat. Biotechnol.*, 16:359-363; Lewin S. R. et al (1999) *J. Virol.*, 73: 6099-6103.

Covalent linking of a molecular beacon probe to a PCR primer is a unique property of Scorpion primers, e.g. Whitcombe D. et al (1999) *Nature Biotech.*, 17: 804-807; Thelwell N. et al (2000) *Nucleic Acids Res.*, 28: 3752-3761. In 'Scorpions,' the 5'-end of a PCR primer is conjugated to the 3'-end of a molecular beacon through a long, flexible linker. The linker is not a template for DNA polymerase, thus precluding extension over the beacon sequence. The genomic part of the molecular beacon is designed to bind to a targeted extension product of the primer to which the probe is covalently linked. Unlike Molecular Beacons, the DNA detection stage in Scorpions becomes an intra-molecular reaction. This helps to overcome yet another problem of the Beacon technology associated with the slow kinetics of hybridization.

Eclipse probes are yet another example of hybridization-based FRET probes that have low fluorescence background (Afonina I. A. et al (2002) *BioTechniques*, 32: 940-949). The Eclipse probe design includes a minor groove binding (MGB) moiety at the 5'-end in addition to two FRET dyes, one of which is a non-fluorescent or dark quencher. Due to the strong, DNA-duplex-stabilizing effects of the MGB-moiety, as discussed in Kutyavin I. V. et al (1997) *Nucleic Acids Res.*, 25: 3718-3723, the probes can be designed to be as short as 12-20-mers while still maintaining the hybridization properties required for real-time PCR detection. Placing the MGB-tail at the 5'-end of the probes completely blocks 5'-nuclease cleavage and the fluorescent signal is generated solely due to the hybridization-triggered dye separation.

The mechanism of FRET disruption by distancing of FRET dyes possesses certain limits. It is difficult, for example, to completely abolish the FRET effect, and the probes have to be at least 20-24-mers. In short 8-12 bp probe-target duplexes, "residual" quenching can reach as much as 20-50% (Cardullo R. A. et al (1988) *Proc. Natl. Acad. Sci. USA*, 85: 8790-8794). Furthermore, the reporter dye can be partially quenched by neighboring bases, in particular, by guanines regardless of little spectral overlap. This effect is well known and has been used in a DNA detection technology known by the name of Self-Quenched Fluorogenic primers or also LUX primers (abbreviation of Light Upon eXtension), e.g. Nazarenko I. et al (2002) *Nucleic Acids Res.*, 30: e37; Nazarenko I. et al (2002) *Nucleic Acids Res.*, 30: 2089-2195. The technology performs best with "green" dyes like fluorescein (FAM). However, LUX primers are not sequence-specific. Any product of a LUX primer extension, including primer-dimers, will generate a fluorescent signal.

Cleavable FRET probes. An effective strategy to abolish FRET is based on cleavage of the oligonucleotide probes upon their binding to target nucleic acids. TaqMan™ technology was developed as a real-time nucleic acid detection method and utilizes the 5'-3' exonuclease activity of *Thermus aquaticus* (Taq) polymerase, e.g. Lie Y. S. and Petropoulos C. J. (1998) *Curr. Opin. Biotech.*, 9:43-48. A dual-labeled FRET probe is designed to anneal to a target sequence located between two PCR primer binding sites. During strand elongation, Taq polymerase cleaves the probe that is hybridized down stream from a primer site releasing the reporter dye from the quencher thus permanently and irreversibly disrupting FRET, e.g. Livak K. J. et al (1995) *PCR Methods and Applications*, 4: 357-362. TaqMan™ probe cleavage is irreversible and signal generated at a given PCR cycle is a sum of signals generated at that particular cycle plus all previous ones. However, elevated fluorescence background of the "classical" TaqMan™ probes overshadows this advantage. Conjugation with an MGB-moiety at the 3'-end leads to significant improvement of this parameter (Kutyavin I. V. et al (2000) *Nucleic Acids Res.*, 28:655-661). Relatively short 12-18-mer MGB-TaqMan™ probes have improved SNP discriminating properties. However, TaqMan™ technology is still tightly bound to PCR performance whereas Cycling Probe Technologies (CPT) are relatively independent.

Cycling Probe Technologies (CPT). Cycling Probe Technologies (CPT) represent an additional detection system that may be used. These reactions are based on continuous cleavage of oligonucleotide probes which bind to a target nucleic acid in a sequence-specific fashion. An appropriate endonuclease recognizes the complex and cleaves the probe while leaving the target strand intact and recycling it for the next round of cleavage. If the hybridized probe is cleaved internally, the cleavage products form weaker hybrids than the original probe and these probe fragments dissociate from the target strand leaving it available for additional rounds of the cleavage reaction. Target recycling means that more than one probe can be cleaved per target molecule. In CPT reactions, the signal is a function of two main variables, target concentration and time. When the target concentration is fixed, the signal grows linearly in time. Reflecting the reaction progress, cleavage slows down and eventually stops when essentially all CPT probes get cleaved. Several system designs have been reported. One approach is based on use of chimeric DNA-RNA probes that are cleaved by RNAse H upon the binding to target DNA, as described in Fong W. et al (2000) *J. Clin. Microbiol.*, 38: 2525-2529; Modruzan Z. et al (2000) *Diagn. Microbiol. Infect. Dis.*, 37: 45-50. These DNA probes are designed to have at least 4-5 ribonucleotides in the middle of the oligonucleotide chain. RNAse H cleaves only the RNA portion of the hybridized probe and the target polynucleotide is recycled to hybridize to another uncleaved probe molecule. Under appropriate conditions, this leads to a cycling of the probe cleavage reaction. Recent discovery and isolation of thermo-stable analogs of RNAse H have allowed combining this DNA detection technology with PCR, as described by, e.g. Harvey J. J. et al (2004) *Anal. Biochem.*, 333: 246-255. The respective FRET probes may be obtained from Takara Bio.

Another CPT approach is based on the substrate specificity of Endonuclease IV from *E. coli*, an AP endonuclease that initiates repair of abasic sites and other related lesions in DNA. A FRET probe and enhancer can collectively form a substrate for the AP endonuclease that simulates a partially degraded abasic site. The enzyme recognizes this artificial substrate and "clips" the 3'-tail of the probe thereby releasing the reporter dye and disrupting FRET. This reaction can be performed in a cycling mode where a high yield of cleaved probe is achieved at nanomolar or even sub-nanomolar target DNA concentrations, as described in Kutyavin I. V. et al (2004) US Patent Application No. 2004/0101893.

In another embodiment, the INVADER™ detection assay may be employed. It utilizes the flap or 5'-endonuclease activity of certain polymerases to cleave two partially overlapping oligonucleotides upon their binding to target DNA. The INVADER™ assay typically consists of two consecutive cycling cleavage reactions. The enzyme used to provide the cleavage reaction is CLEAVASE, a DNA polymerase with substantially reduced or completely eliminated synthetic capabilities, e.g. Dahlberg J. E. et al (1997) U.S. Pat. Nos. 5,691,142; 5,837,450; 5,846,717; 5,985,557; 5,994,069; 6,001,567; 6,090,543; 6,348,314; 6,875,572; 6,913,881; as well as in Schweitzer B. and Kingsmore S. (2001) *Curr. Opin. Biotech.*, 12: 21-27. The detection system is a very efficient signal amplification assay which may not require any prior target DNA amplification. However, prior amplification of nucleic acids is a preferred approach in applying the INVADER assay. Background fluorescence increases linearly with time as a result of non-specific cleavage of the cassette probe. Furthermore the assay requires substantial target DNA load, e.g. Schweitzer B. and Kingsmore S. (2001) *Curr. Opin. Biotech.*, 12: 21-27, when the amplification is not applied. Combinations of CPT with nucleic acid amplification techniques provide advantages, e.g., as described for the oligonucleotide probes with secondary structures in Sorge J. A. (2001) U.S. Pat. No. 6,589,743.

It will be understood by one of ordinary skill in the relevant arts that other suitable modifications and adaptations to the methods, compositions, reaction mixtures and kits described herein are readily apparent from the description of the invention contained herein in view of information known to the ordinarily skilled artisan, and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Examples are provided below illustrating certain aspects and embodiments of the invention. It will be appreciated by the skilled artisan that these examples are not intended to limit the invention to the specific embodiments described therein. Additionally, those skilled in the art, using the techniques, materials and methods described herein, could easily devise and optimize alternative reverse transcription and/or amplification systems for carrying out these and related methods while still being within the spirit and scope of the present invention.

In this example, it is demonstrated that reverse transcriptase enzymes can adopt and use as substrates base-modified dNTPs, and that the incorporation of these base-modified dNTPs into modified cDNA results in improved sensitivity, efficiency and yield during subsequent nucleic acid amplification. Thus, in accordance with the present invention, methods are provided for improved amplification-based detection of RNA sequences by synthesizing modified cDNAs during reverse transcription where the modified cDNAs have incorporated therein base-modified dNTPs.

1. Reverse Transcription

The experimental protocol used for performing reverse transcription is described below. Experiments were run in parallel using either natural or base-modified dNTPs. In the experiments using base-modified dNTPs, a mixture was used comprising 2,6-diaminopurine deoxynucleoside 5'-O-triphosphate (also referred to as d(2-amA)TP), 5-propynyl deoxyuridine 5'-O-triphosphate (also referred to as d(5-PrU)TP), 5-propynyl deoxycytosine 5'-O-triphosphate (also referred to as d(5-PrC)TP) and dGTP. The reaction mixtures were prepared by mixing appropriate stock solutions in amounts indicated below. The forward and reverse primers, as well as the target miRNA sequence, are shown in FIG. 1.

Reverse Transcription:

| Reaction mixture: | Amount: |
|---|---|
| RT primer (reverse primer, 2 μM) | 1 μl |
| Target RNA, miR-155 ($10^8$ copies/μl) | 0.5 μl |
| 10X dNTPs mix (2 mM each of natural or base-modified) | 5 μl |
| Water | 5.5 μl |
| Total volume: | 12 μl |

The reaction mixture was heated to 65° C. for 5 minutes and chilled on ice. Then the following was added:

| 5X First-Strand Buffer (Invitrogen) | 4 μl |
|---|---|
| 0.1 M DTT | 2 μl |
| Water | 1 μl |

(5X First Strand Buffer comprises: 375 mM KCl, 15 mM MgCl2, 0.1 M DTT, 250 mM Tris-HCl (pH8.3))

The reaction mixture was heated to 45° C. for 2 minutes and then 1 μl SuperScript™ II RT (Invitrogen) was added.

The temperature profile used in the RT reaction was to heat at 42° C. for 60 minutes; heat at 95° C. for 2 minutes, and cool to 4° C. for 1 minute.

2. Amplification

Polymerase chain reaction was used to amplify cDNA products resulting from the reverse transcription reaction, using the experimental protocol described below. Natural dNTPs were used in the amplification reaction.

Real Time PCR:

| Reaction mixture: | Amount: | For 15 reactions: |
|---|---|---|
| 10X PCR buffer | 2.5 μl | 37.5 μl |
| 10x dNTPs mix (natural) | 2.5 μl | 37.5 μl |
| Forward Primer (2 μM) | 2.5 μl | 37.5 μl |
| Reverse Primer (2 μM) | 2.5 μl | 37.5 μl |
| 2X SYBR Green | 2.5 μl | 37.5 μl |
| RT-reaction mixture | 2.5 μl | 37.5 μl |
| JumpStart polymerase (1 U/μl) | 1 μl | 15 μl |
| Water | 9 μl | 135 μl |
| Total volume: | 25 μl | 375 μl |

(10x Buffer comprised: 500 mM KCl, 20 mM MgCl2, 200 mM Tris-HCl (pH8.0))

The temperature profile used in the PCR reaction was: 95° C. 2'→(95° C. 10"→56° C. 45")$_{55}$ Primers were designed to be specific to the miRNA target sequence referred to as miR-155, as shown in FIG. 1. The reverse primer was designed for use in the reverse transcription (RT) reaction to produce a cDNA template complementary to miR-155. The reverse primer overlapped with the miR-155 sequence along 8 bases, forming a duplex having a predicted Tm of >45° C.

However, as can be seen in FIG. 1, the forward PCR primer overlaps with the cDNA along 12 bases. Given the small size of the target miR-155, designing this primer to have greater overlap with the target sequence would lead to an overlap with the reverse primer, thus promoting primer-dimer formation during subsequent PCR. Even though the primer sequence in this example contained four modified d(2-amA) TP bases in the overlap region with the target miR-155 sequence, the primer is predicted to form an overlap duplex with cDNA at Tm=~40° C. Typical annealing temperatures used in PCR reactions are in the range ~60-65° C. In the experiments described, an annealing temperature of 56° C. was used. Thus, it would be expected that this 16° C. gap between the PCR annealing temperature and duplex stability of forward primer hybridized to cDNA would lead to a reduction of PCR yield when the cDNA produced by reverse transcription subsequently participates in a PCR reaction.

However, the use of base-modified duplex-stabilizing dNTPs during the reverse transcription reaction was found to improve the yield of cDNA synthesis as well as subsequent PCR amplification. The duplex-stabilizing dNTP mixture used during reverse transcription contained d(2-amA)TP, d(5-PrU)TP, d(5-PrC)TP and dGTP. Subsequent PCR amplification was carried out in the presence of natural dNTPs. The results of these experiments are shown in FIG. 2, which demonstrates that incorporation of base-modified duplex-stabilizing dNTPs during reverse transcription of miR-155 substantially improved subsequent efficiency and sensitivity in the amplification-based detection of this short RNA target sequence.

While the present invention has been described and shown in considerable detail with reference to certain preferred embodiments, those skilled in the art will readily appreciate other embodiments of the present invention. Accordingly, the present invention is deemed to include all modifications and variations encompassed within the spirit and scope of the following appended claims.

The invention claimed is:

1. A method for reverse transcription of a small RNA target sequence less than about 100 nucleotides in length, which comprises:
   (a) contacting a sample comprising the small RNA target sequence with:
      (i) a primer that is sufficiently complementary to the small RNA target sequence to hybridize thereto, and
      (ii) an RNA-dependent DNA polymerase having reverse transcriptase activity; and
   (b) synthesizing cDNA complementary to the small RNA target sequence in the presence of a mixture of dNTPs comprising at least one base-modified, duplex-stabilizing dNTP that is a substrate for the RNA-dependent DNA polymerase.

2. The method of claim 1, where the mixture of dNTPs comprises a base-modified, duplex-stabilizing dNTP that is a pyrimidine substituted at the 5-position.

3. The method of claim 1, where the mixture of dNTPs comprises a base-modified, duplex-stabilizing dNTP having the formula:

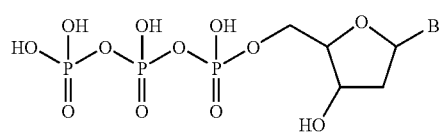

where B is selected from:

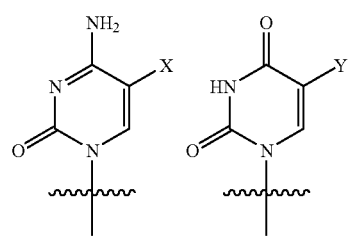

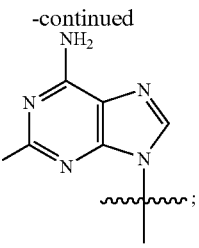

X is selected from —F, —Cl, —Br, —I, —CH$_3$ or $$\equiv\!\!-\!\!CH_2R;$$

Y is selected from —F, —Cl, —Br, —I or $$\equiv\!\!-\!\!CH_2R;$$

and
R is —H, —OH, —OCH$_3$ or —NH$_2$.

4. The method of claim 1, where the mixture of dNTPs comprises a base-modified, duplex-stabilizing dNTP selected from d(2-amA)TP, d(5-PrU)TP and/or d(5-PrC)TP.

5. The method of claim 1, where the mixture of dNTPs comprises at least two of (2-amA)TP, d(5-PrU)TP and d(5-PrC)TP and/or dGTP.

6. The method of claim 1, where the small RNA target sequence is about 10 to 30 nucleotides in length.

7. The method of claim 1, where the small RNA target sequence is a miRNA sequence.

8. The method of claim 1, where the primer has incorporated therein one or more base-modified duplex-stabilizing dNTPs.

9. The method of claim 1, further comprising the steps of:
   (c) treating the cDNA formed in step (b) to provide single-stranded cDNA; and
   (d) contacting the single-stranded cDNA with a second primer that is sufficiently complementary to the cDNA to hybridize thereto and initiate synthesis of an extension product in the presence of a DNA polymerase to produce a double-stranded cDNA molecule.

10. The method of claim 1, further comprising the step of performing a nucleic acid amplification reaction using amplification primers that are sufficiently complementary to the small RNA target sequence and its complement to hybridize thereto and produce amplification products in the presence of DNA polymerase.

11. The method of claim 10, where the nucleic acid amplification reaction is a polymerase chain reaction.

12. The method of claim 10, where one or more of the amplification primers comprises base-modified duplex-stabilizing dNTPs incorporated therein.

13. The method of claim 10, where the amplification reaction is performed in the presence of a mixture of deoxynucleoside 5'-triphosphates containing at least one base-modified duplex-stabilizing dNTP.

14. A reaction mixture comprising:
(a) a sample comprising a small RNA target sequence;
(b) a primer that is sufficiently complementary the small RNA target sequence to hybridize therewith,
(c) an RNA-dependent DNA polymerase having reverse transcriptase activity; and
(d) a mixture of deoxynucleoside 5'-triphosphates containing at least one base-modified duplex-stabilizing dNTP that is a substrate for the RNA-dependent DNA polymerase.

15. The reaction mixture of claim 14, where the mixture of dNTPs comprises a base-modified, duplex-stabilizing dNTP that is a pyrimidine substituted at the 5-position.

16. The reaction mixture of claim 14, where the mixture of dNTPs comprises a base-modified, duplex-stabilizing dNTP having the formula:

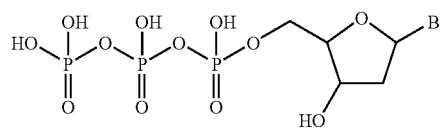

where B is selected from:

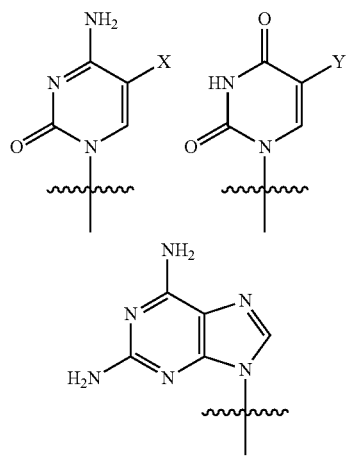

X is selected from —F, —Cl, —Br, —I, —CH$_3$ or

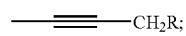

Y is selected from —F, —Cl, —Br, —I or

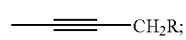

and

R is —H, —OH, —OCH$_3$ or —NH$_2$.

17. The reaction mixture of claim 14, where the mixture of dNTPs comprises a base-modified, duplex-stabilizing dNTP selected from d(2-amA)TP, d(5-PrU)TP and/or d(5-PrC)TP.

* * * * *

SEQUENCE LISTING

<160> NUMBER OF SEQ ID NOS: 3

<210> SEQ ID NO 1
<211> LENGTH: 27
<212> TYPE: DNA
<213> ORGANISM: Artificial Sequence
<220> FEATURE:
<223> OTHER INFORMATION: Forward Primer

<400> SEQUENCE: 1

```
gagaccagca tgcgtttaat gctaatc                                              27

<210> SEQ ID NO 2
<211> LENGTH: 22
<212> TYPE: RNA
<213> ORGANISM: Homo sapien

<400> SEQUENCE: 2
uuaaugcuaa ucgugauagg gg                                                   22

<210> SEQ ID NO 3
<211> LENGTH: 24
<212> TYPE: DNA
<213> ORGANISM: Artificial Sequence
<220> FEATURE:
<223> OTHER INFORMATION: Reverse Primer

<400> SEQUENCE: 3
gctaggatcg agttcccta tcac                                                  24
```